United States Patent
Hu et al.

(10) Patent No.: US 9,377,409 B2
(45) Date of Patent: *Jun. 28, 2016

(54) FABRICATING AN APPARATUS FOR USE IN A SENSING APPLICATION

(75) Inventors: Min Hu, Sunnyvale, CA (US); Zhiyong Li, Foster City, CA (US); Fung Suong Ou, Palo Alto, CA (US); Ansoon Kim, Mountain View, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1129 days.

This patent is subject to a terminal disclaimer.

(21) Appl. No.: 13/194,556

(22) Filed: Jul. 29, 2011

(65) Prior Publication Data
US 2015/0177151 A1    Jun. 25, 2015

(51) Int. Cl.
G01J 3/44 (2006.01)
G01N 21/65 (2006.01)
G01J 3/02 (2006.01)
B82Y 20/00 (2011.01)

(52) U.S. Cl.
CPC ............. G01N 21/658 (2013.01); G01J 3/0256 (2013.01); G01J 3/4412 (2013.01); B82Y 20/00 (2013.01); G01N 2201/06113 (2013.01); Y10S 977/954 (2013.01); Y10T 29/49 (2015.01)

(58) Field of Classification Search
CPC .................................................. G01N 21/658
See application file for complete search history.

(56) References Cited

U.S. PATENT DOCUMENTS

| | | | |
|---|---|---|---|
| 5,677,196 A | 10/1997 | Herron et al. | |
| 6,193,870 B1 | 2/2001 | Morse et al. | |
| 6,222,619 B1 | 4/2001 | Herron et al. | |
| 6,756,795 B2 | 6/2004 | Hunt et al. | |
| 6,777,244 B2 | 8/2004 | Pepper et al. | |
| 7,212,284 B2 | 5/2007 | Deng et al | |

(Continued)

FOREIGN PATENT DOCUMENTS

| | | |
|---|---|---|
| EP | 2058908 | 5/2009 |
| EP | 2128598 | 12/2009 |

(Continued)

OTHER PUBLICATIONS

Baldwin, Jean, Norbert Schuhler, Ian S. Butler, & Mark P. Andrews, "Integrated Optics Evanescent Wave Surface Enhanced Raman Scattering (IO-EWSERS) of Mercaptopyridines on a Planar Optical Chemical Bench: Binding of Hydrogen and Copper Ion", Langmuir, 1996, vol. 12, pp. 6389-6398.

(Continued)

*Primary Examiner* — Kara E Geisel
*Assistant Examiner* — Shawn Decenzo
(74) *Attorney, Agent, or Firm* — Mannava & Kang, P.C.

(57) ABSTRACT

In a method of fabricating an apparatus for use in a sensing application, a plurality of nano-fingers are formed on a substrate and a Raman-active material nano-particle is formed on respective tips of the nano-fingers. In addition, the Raman-active material nano-particles on the tips of adjacent ones of the nano-fingers are caused to come into contact with the Raman-active material nano-particle on the tip of at least another one of the plurality of nano-fingers to form respective clusters and the clusters of Raman-active material nano-particles are transferred to a component layer from the plurality of nano-fingers while maintaining a spatial relationship between the contacting Raman-active material nano-particles.

12 Claims, 5 Drawing Sheets

(56) References Cited

U.S. PATENT DOCUMENTS

| | | | |
|---|---|---|---|
| 7,224,451 B2 | 5/2007 | Naya | |
| 7,256,886 B2 | 8/2007 | Cullum et al. | |
| 7,288,419 B2 | 10/2007 | Naya | |
| 7,342,656 B2 | 3/2008 | Islam et al. | |
| 7,351,588 B2 | 4/2008 | Poponin | |
| 7,463,661 B2 | 12/2008 | Ogura | |
| 7,476,787 B2 | 1/2009 | Thomas et al. | |
| 7,528,948 B2 | 5/2009 | Bratkovski et al. | |
| 7,576,854 B2 | 8/2009 | Wang et al. | |
| 7,583,379 B2 | 9/2009 | Zhao et al. | |
| 7,586,601 B2 | 9/2009 | Ebstein | |
| 7,609,378 B2 | 10/2009 | Konakahara | |
| 7,651,863 B2 | 1/2010 | Hulteen et al. | |
| 7,656,525 B2 | 2/2010 | Zhao et al. | |
| 7,667,238 B2 | 2/2010 | Erchak et al. | |
| 7,707,647 B2 | 4/2010 | Konakahara | |
| 7,833,842 B2 | 11/2010 | Williams et al. | |
| 7,884,930 B2 | 2/2011 | Kirby et al. | |
| 8,462,333 B2 | 6/2013 | Wu et al. | |
| 8,767,202 B2 | 7/2014 | Schmidt et al. | |
| 9,013,689 B2 | 4/2015 | Reinhard et al. | |
| 2001/0006869 A1 | 7/2001 | Okamoto et al. | |
| 2003/0077023 A1 | 4/2003 | Troll | |
| 2004/0135997 A1 | 7/2004 | Chan et al. | |
| 2006/0038990 A1 | 2/2006 | Habib et al. | |
| 2006/0231381 A1 | 10/2006 | Jensen et al. | |
| 2006/0250613 A1 | 11/2006 | Demuth et al. | |
| 2007/0015288 A1 | 1/2007 | Hulteen et al. | |
| 2007/0070341 A1 | 3/2007 | Wang et al. | |
| 2007/0086001 A1 | 4/2007 | Islam et al. | |
| 2007/0115469 A1 | 5/2007 | Ebstein | |
| 2007/0178658 A1 | 8/2007 | Kelley et al. | |
| 2007/0252136 A1 | 11/2007 | Lieber et al. | |
| 2008/0017845 A1 | 1/2008 | Drndic et al. | |
| 2008/0024776 A1 | 1/2008 | Bratkovski et al. | |
| 2008/0079104 A1 | 4/2008 | Stewart et al. | |
| 2008/0098805 A1 | 5/2008 | Jin et al. | |
| 2008/0144026 A1 | 6/2008 | Zhao et al. | |
| 2008/0166706 A1 | 7/2008 | Zhang et al. | |
| 2008/0174775 A1 | 7/2008 | Moskovits et al. | |
| 2008/0187648 A1 | 8/2008 | Hart et al. | |
| 2008/0311028 A1 | 12/2008 | Stanbery | |
| 2009/0117646 A1 | 5/2009 | Stordeur et al. | |
| 2009/0261815 A1 | 10/2009 | Cairns et al. | |
| 2009/0263430 A1 | 10/2009 | Scheibel et al. | |
| 2009/0303472 A1 | 12/2009 | Zhao et al. | |
| 2010/0062226 A1 | 3/2010 | Hulteen et al. | |
| 2010/0085566 A1* | 4/2010 | Cunningham | 356/301 |
| 2010/0149529 A1 | 6/2010 | Biris et al. | |
| 2010/0321684 A1 | 12/2010 | Bratkovski et al. | |
| 2011/0001118 A1 | 1/2011 | Bhupendra et al. | |
| 2011/0030792 A1 | 2/2011 | Miguez et al. | |
| 2011/0053794 A1 | 3/2011 | Zhang | |
| 2011/0116089 A1 | 5/2011 | Schmidt et al. | |
| 2011/0128535 A1* | 6/2011 | Baker et al. | 356/301 |
| 2011/0128537 A1 | 6/2011 | Bond et al. | |
| 2011/0188035 A1 | 8/2011 | Kuo et al. | |
| 2011/0267610 A1* | 11/2011 | Hu et al. | 356/301 |
| 2011/0267614 A1* | 11/2011 | Reinhard et al. | 356/301 |
| 2012/0013903 A1 | 1/2012 | Kuo et al. | |
| 2012/0107948 A1 | 5/2012 | Li et al. | |
| 2012/0113419 A1 | 5/2012 | Wang et al. | |
| 2012/0212732 A1 | 8/2012 | Santori et al. | |
| 2013/0040862 A1* | 2/2013 | Li et al. | 506/20 |
| 2014/0009758 A1* | 1/2014 | Li et al. | 356/301 |

FOREIGN PATENT DOCUMENTS

| | | |
|---|---|---|
| JP | 2000-206048 | 7/2000 |
| TW | 200407536 | 5/2004 |
| WO | WO-2006138442 | 12/2006 |
| WO | WO-2008028130 | 3/2008 |
| WO | WO-2009117646 | 9/2009 |
| WO | WO-2010056258 | 5/2010 |
| WO | WO-2010081088 | 7/2010 |
| WO | WO-2010088585 | 8/2010 |
| WO | WO-2010088726 A1 | 8/2010 |
| WO | WO-2010126640 | 11/2010 |
| WO | WO-2011014176 | 2/2011 |
| WO | WO-2011133143 | 10/2011 |

OTHER PUBLICATIONS

Caldwell, J.D. et al., Plasmonic Nanopillar Arrays for Large-area, High Enhancement Surface-enhanced Raman Scattering Sensors, (Research Paper), Apr. 11, 2011.

Hernandez, C.J. et al., Pillar-deposition Particle Templating: a High-throughput Synthetic Route for Producing Lithoparticles Soft Materials, (Research Paper), 2007, pp. 1-11, vol. 5, No. 1.

Josef Giglmayr, Nano-Finger Electrodes for the Electro-Optical Generation and Tuning of Gratings at Several Wavelengths, <http://www.ipme.ru/ipme/conf/NN2003/NN2003_Abstracts.pdf> Publication Date: Aug. 30, 2003-Sep. 6, 2003.

Montgomery, J. M. et al., "SERS Enhancements via Periodic Arrays of Gold Nanoparticles on Silver Film Structures", <http://www.opticsinfobase.org/abstract.cfm?uri=oe-17/10/8669>, pp. 8669-8675, vol. 17, Issue: 10, 2009.

Yim, T.J. et al. Synthesis of a Gold Nanoparticle Dimer Plasmonic Resonator Through Two-phase-mediated Functionalization <http://iopscience.iop.org/0957-4484/19/43/435605> vol. 19; Issue: 43. Sep. 22, 2008.

Cao, et al., "Enhance Raman Scattering from Individual Semiconductor Nanocones and Nanowires", Physical Review Letters PRL 96, 157402, 2006.

Chen, et al., "Single-Walled Carbon Nanotube Networks Decorated with Silver Nanoparticles: A Novel Graded SERS Substrate", J.Phys. Chem.C2007, vol. 111, No. 44, pp. 16167-16173.

Cubukcu, E., et al., "Plasmonic Laser Antennas and Related Devices", IEEE Journal of Selected Topics in Quantum Electronics, Nov./Dec. 2008, vol. 14, No. 6, pp. 148-1461.

Fan, et al., "Multilayer Silver Nanoparticles Modified Optical Fiber Tip for High Performance SERS Remote Sensing," 217th ECS Meeting—Vancouver, Canada, Apr. 25-30, 2010, Electrochemical Nano/Bio Sensors 2, Abs# 1830.

Fan, J. G. et al., "Integrating Aligned Nanorod Array onto Optical Fibers for SERS Probes," Proc. of SPIE—Nanoengineering: Fabrication, Properties, Optics, and Devices III, vol. 6327, 2006, pp. R-1 to R10.

Gilles, et al., "UV Nanoimprint Lithography with Rigid Polymer Molds", Microelectronic Engineering 86, (2009), pp. 661-664.

Gopinath, et al. "Deterministic aperiodic arrays of metal nanoparticles for surface-enhanced Raman scattering (SERS)." Optics Express 17.5 (Feb. 25, 2009), pp. 3741-3753.

Guieu, Valerie, et al. "Multitip-localized enhanced Raman scattering from a nanostructured optical fiber array." The Journal of Physical Chemistry C 113.3 (2008): pp. 874-881.

He, et al., "Large-Scale Synthesis of Flexible Free-Standing SERS Substrates with High Sensitivity: Electrospun PVA Nanofibers Embedded with Controlled Alignment of Silver Nanoparticles", ACSNANO, vol. 3, No. 12, (2009), pp. 3993-4002.

Hu, et al. "Gold nanofingers for molecule trapping and detection." Journal of the American Chemical Society 132.37 (2010): pp. 12820-12822.

Hu, et al., "Metal Coated Si Nanograss as Highly Sensitive SERS Sensors", Proc. of SPIE, vol. 7312 (2009) pp. 73120I-1-6.

Kaplan David; "Functionalized Silk Materials"; Report Date Jun. 10, 2010; Tufts University, Medford MA.

Krishnamoorthy, Sivashankar, et al., "Combining Micelle Self-assembly with Nanostencil Lithography to Create Periodic/aperiodic Micro-/nanopatterns on Surfaces", Jul. 30, 2008, vol. 20, pp. 3533-3538.

Liang, Y. N., et al. "Micro-ink-jetting of silver nanoparticles on low temperature cofired ceramic substrates for drop-on-demand metallization." Journal of Vacuum Science & Technology B 27.3 (Pub. Year: 2009): pp. 1431-1436.

(56) References Cited

OTHER PUBLICATIONS

Lucotti, et al., "Fiber-optic SERS sensor with optimized geometry," Elsevier, ScienceDirect, Sensors and Actuators B, vol. 121, 2007, pp. 356-364.

Qiu, T. et al., 'Surface-enhanced Raman characteristics of Ag cap aggregates on silicon nanowire array' Nanotechnology 17 5769 doi: 10.1088/0957-4484/17/23/ 010, Nov. 10, 2006.

Ren, Hongliang, et al. "The preparation of optical fibre nanoprobe and its application in spectral detection." Optics & Laser Technology 39.5 (2007): pp. 1025-1029.

Schmidt, et al., "Towards Easily Reproducible Nano-Structured SERS Substrates", IEEE Sensors 2009 Conference, (2009), pp. 1763-1767.

Segawa, H., et al., "Top-gathering pillar array of hybrid organic-inorganic material by means of self-organization", Applied Physics A—Materials Science & Processing, Mar. 17, 2006, vol. 83, pp. 447-451.

Sun, Yinghui, et al., "Highly sensitive surface-enhanced Raman scattering substrate made from superaligned carbon nanotubes." Nano letters 10.5 (2010): pp. 1747-1753.

White, Daniel J., et al. "Nanostructured optical fibre for surface-enhanced Raman scattering sensing." Proc SPIE. vol. 7102. 2008.

Wu, W., et al. "One-kilobit cross-bar molecular memory circuits at 30-nm half-pitch fabricated by nanoimprint lithography." Applied Physics A 80.6 (2005): pp. 1173-1178.

Xie, Z., et al., "Polymer optical fiber SERS sensor with gold nanorods." Optics Communications, vol. 282, No. 3, (2009, pp. 439-442.

Zhang, et al., "Single-Fiber Probe Based on Surface Enhanced Raman Scattering (SERS)," IEEE Sensors, 2005, pp. 1088-1091.

\* cited by examiner

FABRICATING AN APPARATUS FOR USE IN A SENSING APPLICATION

STATEMENT OF GOVERNMENT INTEREST

This invention was made with government support under Contract No. HR0011-09-3-0002, awarded by the Defense Advanced Research Projects Agency. The government has certain rights in the invention.

CROSS-REFERENCE TO RELATED APPLICATION

The present application contains some common subject matter with copending and commonly assigned U.S. patent application Ser. No. 12/905,891, titled "Apparatus for Performing SERS", filed on Oct. 15, 2010, U.S. patent application Ser. No. 13/029,915, titled "Apparatus for Performing SERS", filed on Feb. 17, 2011, and PCT Application No. PCT/US11/29810, titled "Apparatus for use in Sensing Applications", filed on Mar. 24, 2011, the disclosures of which are hereby incorporated by reference in their entireties.

BACKGROUND

Detection and identification or at least classification of unknown substances has long been of great interest and has taken on even greater significance in recent years. Among advanced methodologies that hold a promise for precision detection and identification are various forms of spectroscopy, especially those that employ Raman scattering. Spectroscopy may be used to analyze, characterize and even identify a substance or material using one or both of an absorption spectrum and an emission spectrum that results when the material is illuminated by a form of electromagnetic radiation (for instance, visible light). The absorption and emission spectra produced by illuminating the material determine a spectral 'fingerprint' of the material. In general, the spectral fingerprint is characteristic of the particular material or its constituent elements facilitating identification of the material. Among the most powerful of optical emission spectroscopy techniques are those based on Raman scattering.

Raman scattering optical spectroscopy employs an emission spectrum or spectral components thereof produced by inelastic scattering of photons by an internal structure of the material being illuminated. These spectral components contained in a response signal (for instance, a Raman signal) may facilitate determination of the material characteristics of an analyte species including identification of the analyte.

The Raman signal level or strength may be significantly enhanced by using a Raman-active material (for instance, Raman-active surface), however. For instance, the Raman scattered light generated by a compound (or ion) adsorbed on or within a few nanometers of a structured metal surface can be $10^3$-$10^{12}$ times greater than the Raman scattered light generated by the same compound in solution or in the gas phase. This process of analyzing a compound is called surface-enhanced Raman spectroscopy ("SERS"). In recent years, SERS has emerged as a routine and powerful tool for investigating molecular structures and characterizing interfacial and thin-film systems, and even enables single-molecule detection.

BRIEF DESCRIPTION OF THE DRAWINGS

Features of the present disclosure are illustrated by way of example and not limited in the following figure(s), in which like numerals indicate like elements, in which.

DETAILED DESCRIPTION

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure.

Throughout the present disclosure, the terms "a" and "an" are intended to denote at least one of a particular element. As used herein, the term "includes" means includes but not limited to, the term "including" means including but not limited to. The term "based on" means based at least in part on. In addition, the term "light" refers to electromagnetic radiation with wavelengths in the visible and non-visible portions of the electromagnetic spectrum, including infrared and ultraviolet portions of the electromagnetic spectrum.

Disclosed herein are a method for fabricating an apparatus for use in a sensing application and an apparatus for use in a sensing application. In the method, a plurality of clusters of Raman-active material nano-particles are formed on the tops of a plurality of nano-fingers and transferred to a component layer. The clusters of Raman-active material nano-particles generally form hot-spots of relatively large electric field strength, which generally enhance detection of molecules in sensing applications. In one regard, the formation of the clusters on the nano-fingers enables the hot-spots to have a larger electric field strength as compared with Raman-active material nano-particles that have simply been placed on the component layer because, for instance, the use of the nano-fingers enables the formation of relatively small (less than about 10 nm wide) gaps in the clusters. In addition, by forming the clusters of Raman-active material nano-particles on the nano-fingers and transferring the clusters onto another structure, the clusters may be provided on structures other than those upon which the nano-fingers are able to be formed.

In the method, physical features that are to enhance Raman signals emitted from molecules located near the clusters of Raman-active material nano-particles may also be formed in the component layer. In addition, the apparatus for use in a sensing application disclosed herein may be implemented as part of a sensing apparatus having an illumination source and a detector.

Figure 1A:
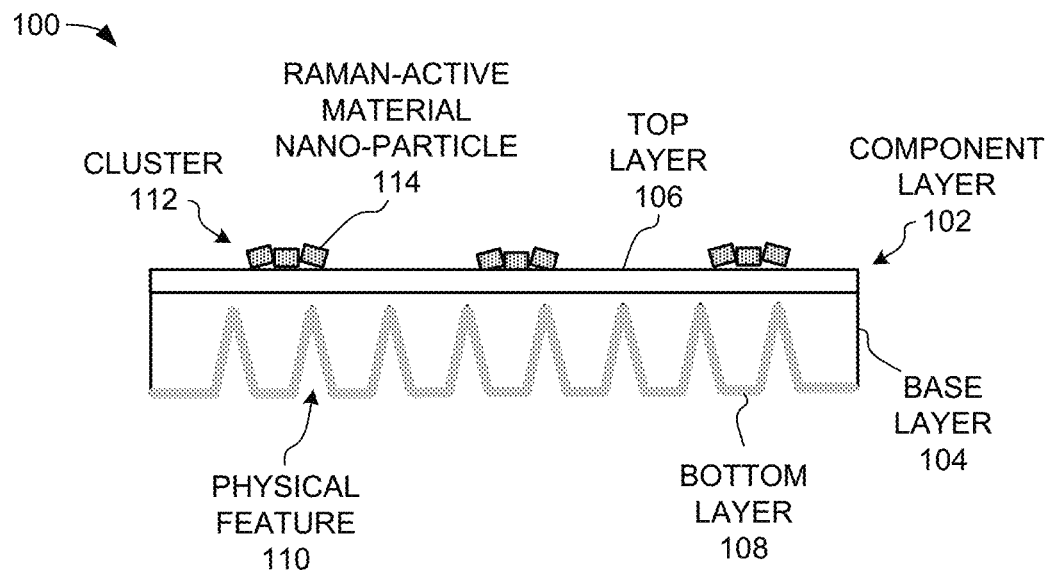
FIGS. 1A and 1B, respectively, show side views of an apparatus for use in a sensing application, according to examples of the present disclosure.

FIG. 1A shows a side view of an apparatus 100 for use in a sensing application, according to an example. It should be understood that the apparatus 100 depicted in FIG. 1A may include additional elements and that some of the elements described herein may be removed and/or modified without departing from a scope of the apparatus 100. It should also be understood that the elements depicted in FIG. 1A are not drawn to scale and thus, the elements may have different relative sizes with respect to each other than as shown therein.

According to an example, the sensing application for which the apparatus 100 is to be used includes, for instance, a sensing application to detect a molecule in an analyte sample with a relatively high level of sensitivity. For instance, the apparatus 100 may be employed in surface enhanced Raman spectroscopy (SERS), enhanced fluorescence, enhanced luminescence, etc., types of applications.

The apparatus 100 is depicted as including a component layer 102 formed of a base layer 104, a top layer 106, and a bottom layer 108. According to an example, the base layer 104 comprises a dielectric material or other type of material, such as, glass, plastic, polymer, $SiO_2$, $Al_2O_3$, etc. In addition, the top layer 106 and the bottom layer 108 comprise a metal material such as, gold, silver, copper, platinum, aluminum, etc., or a combination of these metals in the form of alloys.

The base layer 104 is also depicted as including a plurality of physical features 110, in this instance, inverted cones, formed in the base layer 104. The physical features 110 may be formed into the base layer 104 through any suitable process, such as, etching, lithography, stamping, etc. In addition, the bottom layer 108 may follow the contours of the physical features 110. In one regard, the physical features 110 are to enhance Raman signals emitted from molecules located near the clusters 112 of Raman-active material nano-particles 114.

Figure 1B:
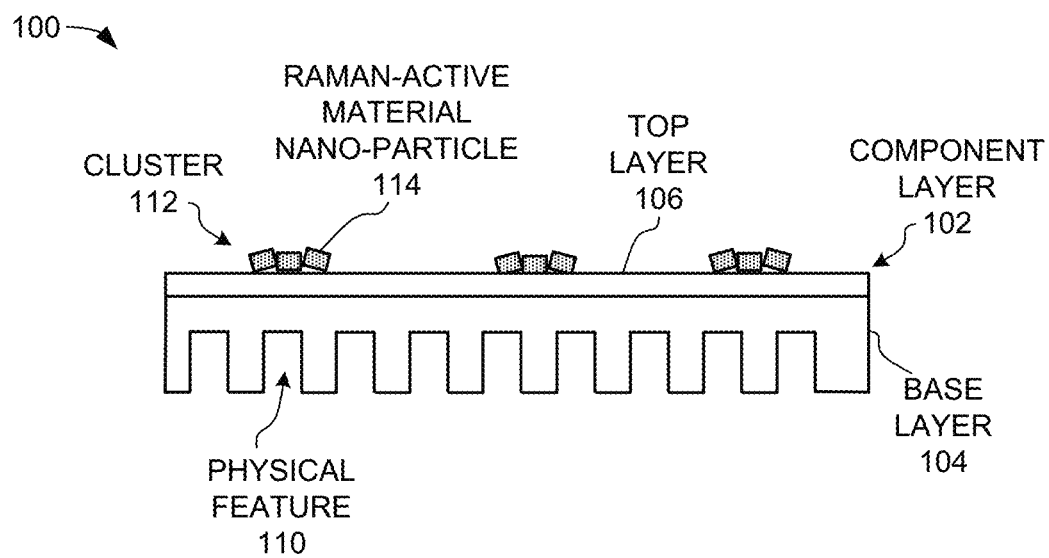

With reference now to FIG. 1B, the component layer 102 is depicted as including gratings formed into the base layer 104. Again, the physical features 110 in the apparatus 100 depicted in FIG. 1B may be formed through any suitable process, such as, etching, lithography, etc. Although FIGS. 1A and 1B depict particular types of physical features 110, it should be understood that the physical features 110 may include other shapes or designs without departing from a scope of the apparatus 100. For instance, the physical features 110 may comprise multiple different shapes across the base layer 104, rounded shapes, other polygonal shapes, etc.

The apparatus 100 depicted in FIGS. 1A and 1B is also shown as including a plurality of clusters 112 of Raman-active material nano-particles 114 on the component layer 102. The Raman-active material nano-particles 114 comprise a metal, such as, gold, silver, copper, platinum, aluminum, etc., or a combination of these metals in the form of alloys, or other suitable material that is able to support surface plasmons for field enhancement for Raman scattering. In addition, the Raman-active material nano-particles 114 may be multilayer structures, for example, 10 to 100 nm silver layer with 1 to 50 nm gold over-coating, or vice versa. By definition herein, a Raman-active material is a material that supports surface plasmons and facilitates Raman scattering from an analyte adsorbed on or near a surface layer of the material during Raman spectroscopy. According to an example, the Raman-active material nano-particles 114 and the top layer 106 are formed of the same metal material.

In some examples, a surface of the Raman-active material nano-particles 114 may be functionalized to facilitate adsorption of an analyte. For example, the Raman-active material nano-particles 114 may be functionalized with a binding group to facilitate binding with a specific target analyte species. The functionalized surface of the Raman-active material nano-particles 114 may provide a surface to which a particular class of analytes is attracted and may bond or be preferentially adsorbed. The functionalized surface may selectively bond with protein, DNA or RNA, for example. In addition, or alternatively, a probe molecule may be sandwiched between the Raman-active material nano-particles 114 in respective clusters 112. In one example, the probe molecule may be selected to interact with certain types of analyte and thus may be used to detect the presence of the certain types of analyte. In another example, the probe molecule may interact with analyte molecules to cause the analyte molecules to emit Raman signals having a relatively higher intensity.

According to an example, the Raman-active material nano-particles 114 in each of the clusters 112 are attached to each other with a gap between at least two of the Raman-active material nano-particles 114 being less than about 10 nm in width. More particularly, the Raman-active material nano-particles 114 in each of the clusters 112 are attached to each other with a gap being less than between about 0.5 nm and 5 nm. Generally speaking, the relatively small gaps between the Raman-active material nano-particles 114 in each of the clusters 112 may be achieved through implementation of the fabrication method disclosed herein. In other words, the fabrication method disclosed herein generally enables the Raman-active material nano-particles 114 to be relatively closer to each other than may be possible through direct formation of the Raman-active material nano-particles 114 on the component layer 102. In addition, the fabrication method disclosed herein may also enable the placement of the clusters 112 of Raman-active material nano-particles 114 to be more accurately controlled.

Figure 1C:
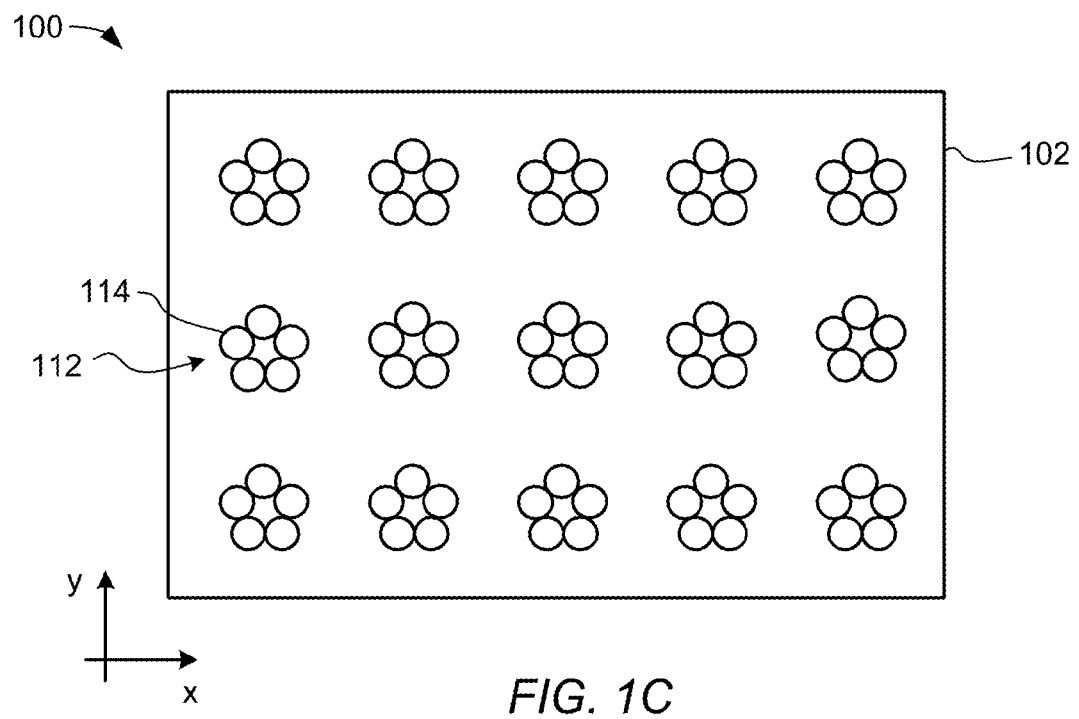
FIGS. 1C and 1D, respectively, show arrangements of a plurality of clusters of Raman-active material nano-particles, according to examples of the present disclosure.
Figure 1D:
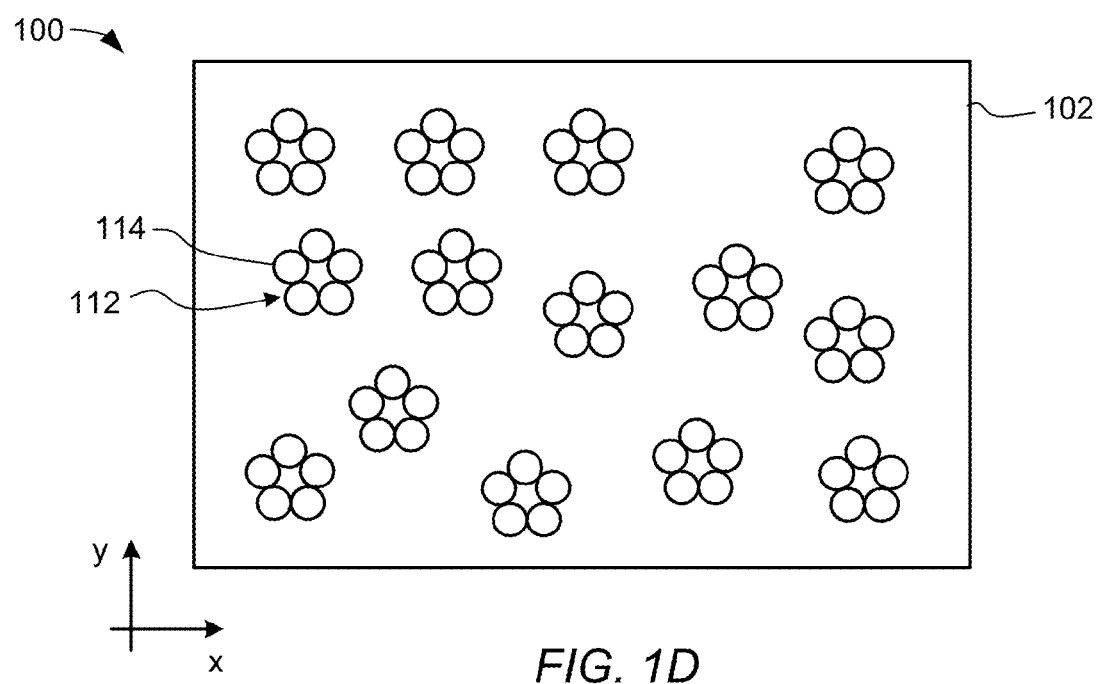

The clusters 112 may include any reasonably suitable number of Raman-active material nano-particles 114 arranged in any suitable spatial configuration. For instance, the clusters 112 may each include two, three, four, five, six, etc., Raman-active material nano-particles 114 arranged in a dimer, trimer, tetramer, pentamer, septamer, etc., configuration. In addition, different ones of the clusters 112 may include different numbers of Raman-active material nano-particles 114 arranged in different configurations with respect to each other. Moreover, the clusters 112 may be arranged in any suitable configuration on the component layer 102. For instance, and as shown in FIG. 1C, the clusters 112 may be arranged in a periodic configuration. Alternatively, as shown in FIG. 1D, the clusters 112 may be arranged in an aperiodic configuration respect to each other, such that, there is no periodicity in the x and y dimensions. In other words, if the patterns of clusters 112 are shifted in the x or y directions, the shifted patterns may not be overlaid with the original pattern. The clusters 112 may also be arranged in relatively more complex aperiodic arrangements that substantially maximize coverage of the clusters 112 on the component layer 102 without forming a periodic configuration. An example of a relatively more complex aperiodic arrangement of clusters is disclosed in the PCT Application No. PCT/US11/29810.

Figure 2:
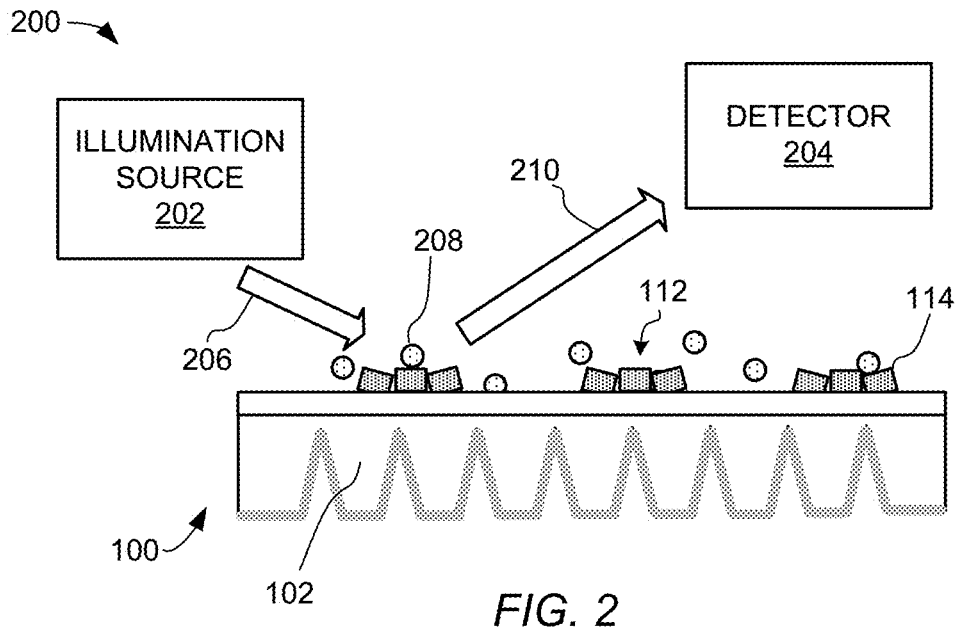
FIG. 2 shows a block diagram of an apparatus for use in a sensing application, according to an example of the present disclosure.

With reference now to FIG. 2 there is shown a block diagram of an apparatus 200 for use in a sensing application, according to an example. It should be understood that the apparatus 200 may include additional elements and that some of the elements described herein may be removed and/or modified without departing from the scope of the apparatus 200. It should also be understood that the elements depicted in the apparatus 200 are not drawn to scale and thus, the elements may have different relative sizes with respect to each other than as shown therein.

As shown in FIG. 2, the apparatus 200 includes the apparatus 100 depicted in FIGS. 1A-1D, an illumination source 202 and a detector 204. An analyte molecule 208 to be tested is depicted as being positioned on a cluster 112 of Raman-active material nano-particles 114. In various instances, the analyte molecule 208 may enter into a gap between the Raman-active material nano-particles 114. In other instances, the analyte molecule 208 may have been introduced between the Raman-active material nano-particles 114 of a cluster 112 prior to the Raman-active material nano-particles 114 being attached to each other. Additional analyte molecules 208 have been depicted as being present around the clusters 112.

The illumination source 202 is depicted as emitting electromagnetic radiation, as represented by the arrow 206, which may comprise, for instance, light. By way of example, the illumination source 202 may comprise a laser that illuminates the Raman-active material nano-particles 114 and the analyte molecules 208. Illumination of the Raman-active material nano-particles 114 causes hot spots of relatively large electric field strength to occur. The hot spots are increased at the locations where the Raman-active material nano-particles 114 contact each other, in this example, the clusters 112. The electric fields generated at the contact locations between the Raman-active material nano-particles 114 generally enhance the rate at which Raman light is scattered by an analyte molecule 208 positioned at or near the contact locations. The Raman scattered light, which is represented by the arrow 210, is shifted in frequency by an amount that is characteristic of particular vibrational modes of the analyte molecule 208. The detector 204 is to collect the Raman scattered light 210 and spectral analysis may be performed on the Raman scattered light 210 to identify the analyte molecule 208 or to detect that the analyte molecule 208 has been illuminated.

The Raman-active material nano-particles 114 located near or adjacent to the analyte molecule(s) 208 may enhance the production of Raman scattered light 210 from the analyte molecule(s) 208 by concentrating or otherwise enhancing an electromagnetic field in a vicinity of the analyte molecule(s) 208. As also discussed above, the contacting of two or more of the Raman-active material nano-particles 114 with each other may trap the analyte molecule(s) 208, which may substantially increase the likelihood that the analyte molecule(s) 208 will be positioned near or in contact with some Raman-active material nano-particles 114 and thus be positioned within a hot spot. In this regard, the likelihood that an analyte molecule(s) 208 will produce sufficiently strong Raman scattered light 210 to be detected by the detector 204 will thus also be increased. In addition, each of the clusters 112 forms a hot spot and thus, the likelihood of detecting an analyte molecule 208 may be relatively high.

Although the Raman scattered light 210 has been depicted as being directed toward the detector 204, the Raman scattered light 210 is emitted in multiple directions. In this regard, some of the Raman scattered light 210 may be directed into the component layer 102, which may comprise an optical waveguide. More particularly, for instance, Raman scattered light 210 may be generated in the component layer 102 as a result of the analyte molecule 208 coupling to the evanescent field of a waveguide mode. In these instances, the detector 204 may be positioned to detect the waves generated in the component layer 102 from the Raman scattered light 210. In any regard, the detector 204 may include a filter to filter out light originating from the illumination source 202, for instance, through use of a grating-based monochrometer or interference filters. Various examples in which the component layer 102 comprises an optical waveguide are described in the Ser. No. 13/029,915 application for patent.

The detector 204 is generally to convert the Raman scattered light 210 emitted from the analyte molecule(s) 208 into electrical signals that may be processed to identify, for instance, the analyte molecule 208 type. In some examples, the detector 204 is to output the electrical signals to other components (not shown) configured to process the electrical signals. In other examples, the detector 204 is equipped with processing capabilities to identify the analyte molecule 208 type.

According to an example, the apparatus 200 comprises a system that is integrated on a single chip. For example, the output of the component layer 102 may be connected to an arrayed waveguide grating (AWG filter). The component layer 102 may also be directly coupled to optical fibers in the apparatus 200 through which the illumination light 206 may be supplied and through which the Raman scattered light 210 may be outputted. In this example, the apparatus 200 provides a relatively more compact solution than coupling free-space signals to fibers. Additionally, the apparatus 200 may be implemented efficiently for a relatively large sensing area for which the free-space signals are substantially more complex and/or expensive to implement. The component layer 102 may also be directly coupled to optical fibers in particular instances to form compact field sensors. In this instance, the illumination source 202, for instance an excitation laser, and the detector 204, for instance spectral analysis equipment, may be housed in a remote location.

Figure 3:
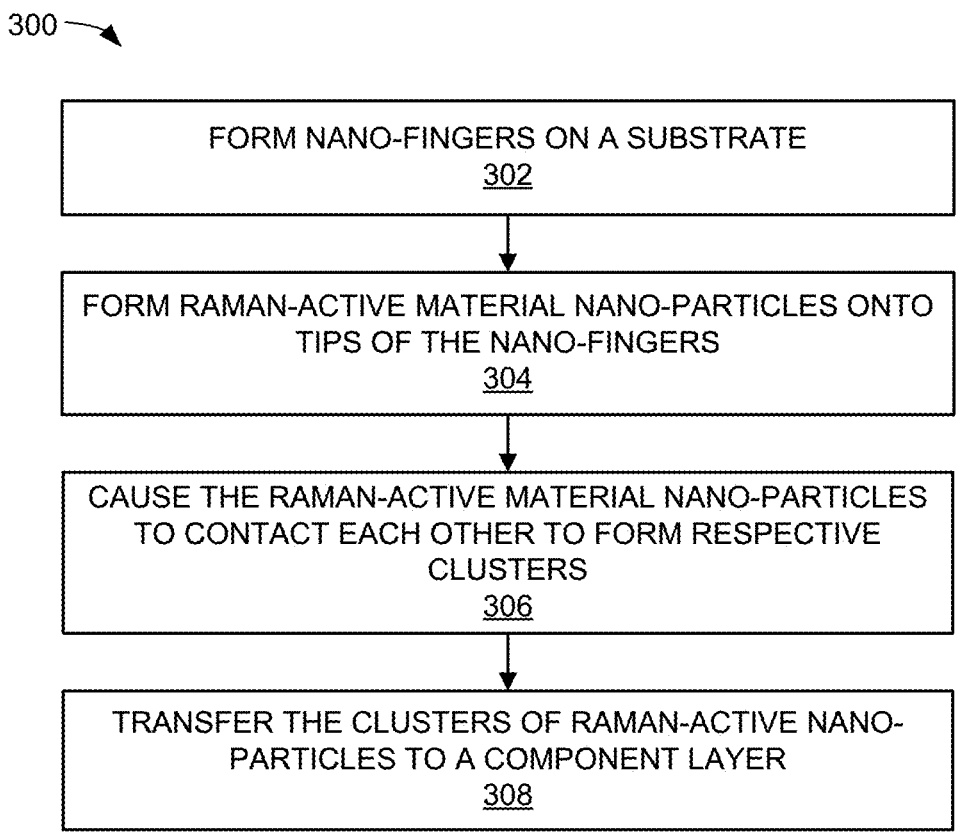
FIG. 3 shows a flow diagram of a method for fabricating an apparatus for use in a sensing application, according to an example of the present disclosure.

Turning now to FIG. 3, there is shown a flow diagram of a method 300 for fabricating an apparatus for use in a sensing application, according to an example. It should be understood that the method 300 may include additional processes and that some of the processes described herein may be removed and/or modified without departing from a scope of the method 300. The method 300 is also described with respect to the fabrication apparatus 400 depicted in FIGS. 4A-4E, which respectively show features of the operations implemented in the blocks of the method 300 to fabricate the apparatus 100.

At block 302, a plurality of nano-fingers 404 (FIG. 4A) are formed on a substrate 102. According to an example, the nano-fingers 404 are formed in a predetermined arrangement on the substrate 102 to substantially cause clusters 112 of the Raman-active material nano-particles 114 to have a predetermined spatial configuration. In addition, the nano-fingers 104 may be formed in the predetermined arrangement to substantially cause the clusters 112 to have a predetermined spatial configuration with respect to each other. According to an example, a nanoimprinting technique or a roll-to-roll process may be implemented to form the nano-fingers 404 on the substrate 402. In this example, a template may be formed through photolithography or other advanced lithography with the desired patterning to arrange the nano-fingers 404 in the predetermined arrangement. More particularly, for instance, the desired patterns may be designed on a mold, by E-beam lithography, photolithography, laser interference lithography, FIB (Focused Ion Beam), self-assembly of spheres, etc. In addition, the pattern may be transferred onto, for instance, silicon, glass, or polymer substrate (PDMS, polyimide, polycarbonate, etc.). In other examples, the nano-fingers 404 may be formed in the predetermined arrangement through implementation of any suitable fabrication process.

The substrate 402 generally comprises any suitable material to support the nano-fingers 404, such as, glass, plastic, polymer, $SiO_2$, $Al_2O_3$, metal, etc. The nano-fingers 404 may be attached to the surface of the substrate 402 through any suitable attachment mechanism. For instance, the nano-fingers 404 may be grown directly on the substrate 402 surface through use of various suitable nano-structure growing techniques. As another example, the nano-fingers 404 may be integrally formed with the substrate 402. In this example, for instance, a portion of the material from which the substrate 402 is fabricated may be etched or otherwise processed to form the nano-fingers 404. In a further example, a separate layer of material may be adhered to the substrate 402 surface and the separate layer of material may be etched or otherwise processed to form the nano-fingers 404.

The nano-fingers 404 are formed of a relatively flexible material to enable the nano-fingers 404 to be laterally bendable, for instance, to enable free ends of the nano-fingers 404 to move toward each other, as discussed in greater detail herein below. Examples of suitable materials for the nano-fingers 404 include polymer materials, such as, polydimethylsiloxane (PDMS) elastomer, polyimide, polyethylene, polypropelene, etc., or any combination thereof, metallic materials, such as, gold, silver, aluminum, etc., semiconductor materials, etc., and combinations thereof. In various examples, the nano-fingers 404 may be fabricated through a nanoimprinting or embossing process in which a template of relatively rigid pillars is employed in a multi-step imprinting process on a polymer matrix to form the nano-fingers 404. Various other processes, such as, etching, and various techniques used in the fabrication of micro-electromechanical systems (MEMS) and nano-electromechanical systems (NEMS) may also be used to fabricate the nano-fingers 404.

A nano-finger 404 may be defined as an elongated, nanoscale structure having a length (or height) that exceeds by more than several times a nanoscale cross sectional dimension (for instance, width) taken in a plane perpendicular to the length (for instance, length>3×width). In general, the length is much greater than the width or cross sectional dimension to facilitate bending of the nano-finger 404 laterally onto one or more neighboring nano-fingers 404. In some examples, the length exceeds the cross sectional dimension (or width) by more than a factor of about 5 or 10. For example, the width may be about 100 nanometers (nm) and the height may be about 500 nm. In another example, the width at the base of the nano-finger 404 may range between about 10 nm and about 1 micrometer ($\mu$m) and the length may range between about 50 nm and 2 $\mu$m. In other examples, the nano-finger 404 is sized based upon the types of materials used to form the nano-finger 404. Thus, for instance, the more rigid the material(s) used to form the nano-finger 404, the less the width of the nano-finger 104 may be to enable the nano-finger 404 to be laterally collapsible. In further examples, the nano-finger 404 may form ridges in which two of three dimensions (for instance length and height) exceed by more than several times a nanoscale cross sectional dimension (for instance, width). According to particular examples, the nano-fingers 404 may equivalently be referenced as nanopoles or nanopillars without departing from a scope of the fabrication apparatus 400.

According to an example, the nano-fingers 404 are arranged with respect to each other on the substrate 402 such that the free ends of at least respective neighboring groups of nano-fingers 404 are able to touch each other when the nano-fingers 404 are in a collapsed state. By way of particular example, groups of neighboring nano-fingers 104 are positioned between about 10 to 500 nm apart from each other.

The nano-fingers 404 have been depicted as having substantially cylindrical cross-sections. It should, however, be understood that the nano-fingers 404 may have other shaped cross-sections, such as, for instance, rectangular, square, triangular, etc. In addition, or alternatively, the nano-fingers 404 may be formed with one or more features, such as, notches, bulges, etc., to substantially cause the nano-fingers 404 to be inclined to collapse in a particular direction. Thus, for instance, two or more adjacent nano-fingers 404 may include the one or more features to increase the likelihood that the nano-fingers 404 collapse toward each other. Various manners in which the nano-fingers 404 may be collapsed are described in greater detail herein below.

Figure 4A:
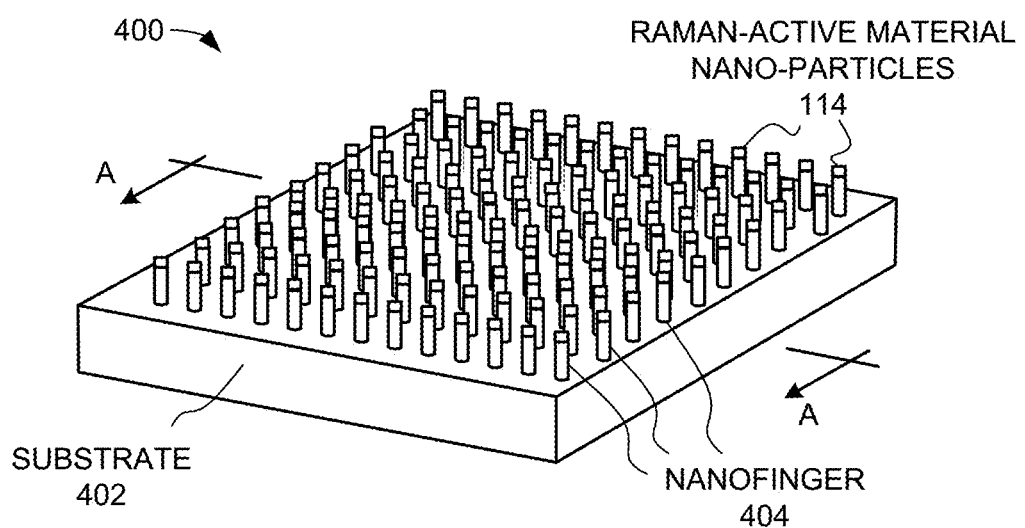
FIGS. 4A-4E, respectively, show features of the operations implemented in the method depicted in FIG. 3, according to an example of the present disclosure.
Figure 4B:
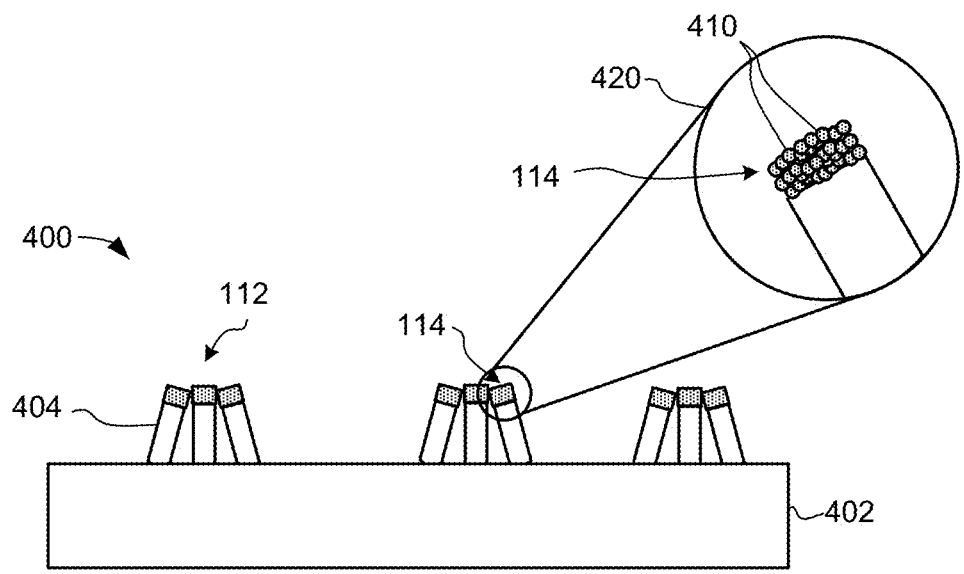

At block 304, respective Raman-active material nano-particles 114 are formed on the tips of the nano-fingers 404. FIG. 4B shows a cross-sectional view along a line A-A, shown in FIG. 4A, of the fabrication apparatus 400, according to an example. In addition, a free end of a nano-finger 404 is magnified in an enlargement 420, which reveals that the Raman-active material nano-particles 114 may be formed of a collection of atoms or atom clusters 410. In addition, although the Raman-active material nano-particle 114 has been depicted as having a rough surface, the Raman-active material nano-particle 114 may comprise a continuous layer of the Raman-active material and may have a relatively smooth surface. Moreover, the Raman-active material nano-particles 114 may have various other shapes than those depicted in FIG. 4B. For instance, the Raman-active material nano-particles 114 may have rounded edges, extend beyond an outer perimeter of the nano-fingers 404, etc.

The atoms or atom clusters 110 may be deposited onto the free ends of the nano-fingers 404 through, for instance, physical vapor deposition (PVD), chemical vapor deposition (CVD), sputtering, etc., of metallic material, or self-assembly of pre-synthesized nano-particles. By way of example, the angle at which the atoms or atom clusters 110 are deposited onto the free second ends of the nano-fingers 404 may be controlled to thereby substantially control the deposition of the atoms or atom clusters 110.

At block 306, the Raman-active material nano-particles 114 on the tips of adjacent ones of the nano-fingers 404 are caused to contact each other to form respective clusters 112. According to an example, the nano-fingers 404 may initially be in a first position, in which their free ends are in a substantially spaced arrangement with respect to each other as shown in FIG. 4A. The gaps between the free ends may be of sufficiently large size to enable a liquid to be supplied in the gaps. In addition, the gaps may be of sufficiently small size to enable the free ends of the nano-fingers 404 in the respective clusters 112 to move toward each other as the liquid evaporates, through, for instance, capillary forces applied on the free ends as the liquid dries. Other non-limiting examples, such as e-beam, ion-beam, magnetic, mechanical force, thermal effect, or electric charge effect, may also or instead be utilized to cause the ends of the nano-fingers 104 to move toward each other. In any regard, the Raman-active material nano-particles 114 in the respective clusters 112 may contact each other and remain in contact with each other through, for instance, van der Waals interactions between those contacting nano-particles 114.

According to an example, a spacer is introduced between the nano-fingers 404 prior to block 306 to space the nano-particles 114 from each other during the cluster formation process. In this example, the spacer may be a sacrificial molecule or material layer that will be bridged in between neighboring finger 404 tips, after the transfer at block 308, this molecule may be washed away or plasma etched, or ozone treated, or may be selectively removed by other proper physical/chemical treatment.

In addition, or alternatively, according to an example, an analyte 208 to be tested using the apparatus 100 is included in the liquid to thus enable molecules from the analyte 208 to be trapped between the Raman-active material nano-particles 114 of respective clusters 112. In addition or alternatively, probe molecules that are to interact with certain types of analytes to enhance detection of the analyte molecules may be included in the liquid to enable the probe molecules to be trapped between the Raman-active material nano-particles 114 of respective clusters 112.

According to another example, the Raman-active material nano-particles 114 may be formed on the tips of the nano-fingers 404 following the closing of the tips in the clusters 112. In this example, blocks 304 and 306 may be reversed with respect to each other.

Figure 4C:
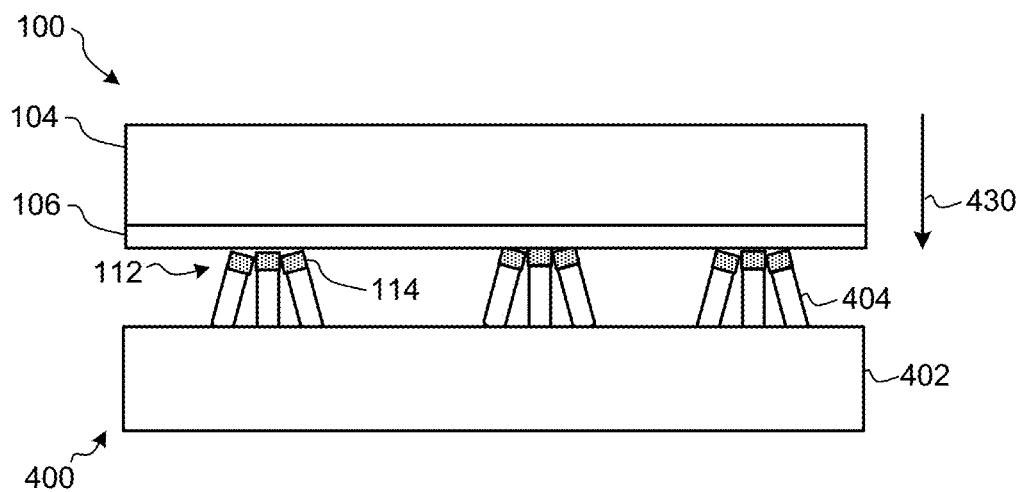

At block 308, the clusters 112 of Raman-active material nano-particles 114 are transferred to a component layer 102. According to an example, the clusters 112 of the Raman-active material nano-particles 114 are transferred to the top layer 106 of the component layer 102, for instance, as shown in FIG. 4C. More particularly, the component layer 102 is moved toward the fabrication apparatus 400 as indicated by the arrow 430 to cause the top layer 106 to contact the clusters 112 of the Raman-active material nano-particles 114. The clusters 112 of the Raman-active material nano-particles 114 may bond to the top layer 106, for instance, through van der Waals interactions between the Raman-active material nano-particles 114 and the top layer 106. In one example, the Raman-active material nano-particles 114 and the top layer 106 may be formed of the same metal material, for instance, gold, platinum, silver, etc., and may become bonded together. In another example, an adhesive material may be provided between the Raman-active material nano-particles 114 and the top layer 106 to cause the Raman-active material nano-particles 114 to adhere to the top layer 106. In a further example, a self-assembled monolayer of functional molecules, such as thiol-terminated silane molecule, may be formed on the surface of the top layer 106 to provide chemical bonding between thiol and the Raman-active material nano-particles 114, and therefore ensure the transfer of the Raman-active material nanoparticles 114 to the top layer 106.

Figure 4D:
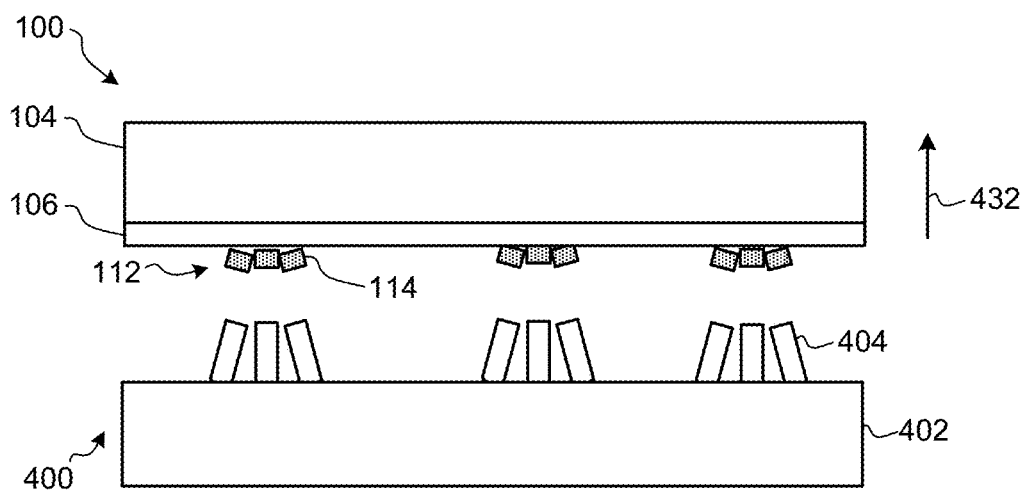

In any regard, following contacting of the top layer 106 to the Raman-active material nano-particles 114 and following adhesion therebetween, the component layer 102 is moved away from the fabrication apparatus 400, as indicated by the arrow 432 (FIG. 4D). As shown in FIG. 4D, clusters 112 of Raman-active material nano-particles 114 are "plucked" off the nano-fingers 404. In one regard, the attraction/adhesion between the Raman-active material nano-particles 114 and the top layer 106 is stronger than the attraction/adhesion between the Raman-active material nano-particles 114 and the nano-fingers 104 because, for instance, the Raman-active material nano-particles 114 and the top layer 106 are made of the same metal material.

Figure 4E:
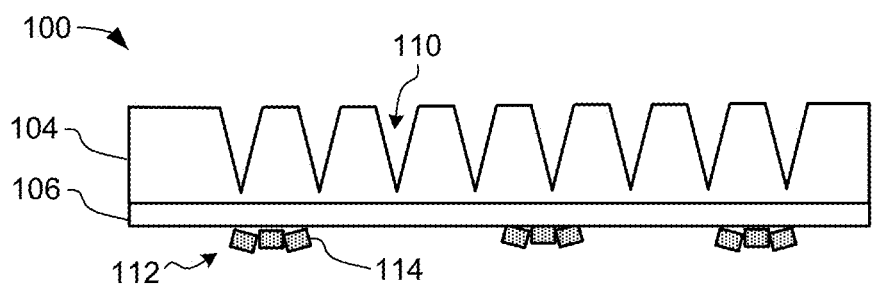

According to an example, physical features 110 are formed in the base layer 104 of the component layer 102, for instance, as shown in FIG. 4E. As discussed above with respect to FIGS. 1A and 1B, the physical features 110 may comprise various different shapes and may be formed through various fabrication techniques. In addition, although the physical features 110 have been depicted as being formed following the transfer of the clusters 112 of Raman-active material nano-particles 114 onto the component layer 102, the physical features 110 may be formed prior to the transfer of the clusters 112 without departing from a scope of the method 300. Moreover, additional fabrication operations may be performed on the apparatus 100, for instance, the bottom layer 108 may be applied to the base layer 104 following formation of the physical features 110.

Although described specifically throughout the entirety of the instant disclosure, representative examples of the present disclosure have utility over a wide range of applications, and the above discussion is not intended and should not be construed to be limiting, but is offered as an illustrative discussion of aspects of the disclosure.

What has been described and illustrated herein is an example along with some of its variations. The terms, descriptions and figures used herein are set forth by way of illustration only and are not meant as limitations. Many variations are possible within the spirit and scope of the subject matter, which is intended to be defined by the following claims—and their equivalents—in which all terms are meant in their broadest reasonable sense unless otherwise indicated.

What is claimed is:

1. A method of fabricating an apparatus for use in a sensing application, said method comprising:
    forming a plurality of nano-fingers on a substrate;
    forming a Raman-active material nano-particle on respective tips of the nano-fingers;
    causing the Raman-active material nano-particles on the tips of adjacent ones of the nano-fingers to come into contact with the Raman-active material nano-particle on the tip of at least another one of the plurality of nano-fingers to form respective clusters; and
    transferring the clusters of Raman-active material nano-particles to a component layer having a top layer from the plurality of nano-fingers while maintaining a spatial relationship between the contacting Raman-active material nano-particles, wherein transferring the Raman-active material nano-particles includes:
        contacting the top layer onto the clusters of Raman-active material nano-particles, causing the clusters of Raman-active material nano-particles to adhere to the top layer; and
        separating the component layer, with the clusters of Raman-active material nano-particles attached, from the plurality of nano-fingers, thereby separating the clusters of Raman-active material nano-particles from the plurality of nano-fingers.

2. The method according to claim 1, wherein causing the Raman-active material nano-particles on the tips of adjacent ones of the nano-fingers to come into contact with Raman-active material nano-particle on the tip of another one of the plurality of nano-fingers further comprises supplying a liquid into gaps between the tips of the plurality of nano-fingers, and wherein evaporation of the liquid causes the tips of the plurality of nano-fingers to approach each other through capillary force.

3. The method according to claim 2, wherein the liquid comprises a plurality of probe molecules, wherein the plurality of probe molecules are to become trapped between the contacting Raman-active material nano-particles.

4. The method according to claim 1, wherein forming the plurality of nano-fingers on the substrate further comprises forming the plurality of nano-fingers in a predetermined arrangement to substantially cause clusters of the Raman-active material nano-particles to have a predetermined spatial configuration.

5. The method according to claim 4, wherein forming the plurality of nano-fingers further comprises:
    forming a template defining the predetermined arrangement of the plurality of nano-fingers;
    transferring the template to the substrate; and
    implementing a fabrication process to form the plurality of nano-fingers in the predetermined arrangement on the substrate.

6. A method of fabricating an apparatus for use in a sensing application, said method comprising:
    forming a plurality of nano-fingers on a substrate;
    forming a Raman-active material nano-particle on respective tips of the nano-fingers;
    causing the Raman-active material nano-particles on the tips of adjacent ones of the nano-fingers to come into contact with the Raman-active material nano-particle on the tip of at least another one of the plurality of nano-fingers to form respective clusters; and transferring the clusters of Raman-active material nano-particles to a component layer having a top layer from the plurality of nano-fingers while maintaining a spatial relationship between the contacting Raman-active material nano-particles, wherein the top layer and the Raman-active material nano-particles are composed of the same material.

7. The method according to claim 6, wherein causing the Raman-active material nano-particles on the tips of adjacent ones of the nano-fingers to come into contact with Raman-active material nano-particle on the tip of another one of the plurality of nano-fingers further comprises supplying a liquid into gaps between the tips of the plurality of nano-fingers, and wherein evaporation of the liquid causes the tips of the plurality of nano-fingers to approach each other through capillary force.

8. The method according to claim 7, wherein the liquid comprises a plurality of probe molecules, wherein the plurality of probe molecules are to become trapped between the contacting Raman-active material nano-particles.

9. A method of fabricating an apparatus for use in a sensing application, said method comprising:

forming a plurality of nano-fingers on a substrate;

forming a Raman-active material nano-particle on respective tips of the nano-fingers;

causing the Raman-active material nano-particles on the tips of adjacent ones of the nano-fingers to come into contact with the Raman-active material nano-particle on the tip of at least another one of the plurality of nano-fingers to form respective clusters;

transferring the clusters of Raman-active material nano-particles to a component layer having a top layer from the plurality of nano-fingers while maintaining a spatial relationship between the contacting Raman-active material nano-particles; and forming physical features into a base layer of the component layer, wherein the physical features are to enhance Raman light emission from molecules positioned near the clusters of Raman-active material nano-particles.

10. The method according to claim 9, wherein the component layer is formed of a dielectric material, said method further comprising:

applying a bottom layer on the component layer on a side opposite from the Raman-active material nano-particles, wherein the bottom layer comprises a metal.

11. The method according to claim 9, wherein causing the Raman-active material nano-particles on the tips of adjacent ones of the nano-fingers to come into contact with Raman-active material nano-particle on the tip of another one of the plurality of nano-fingers further comprises supplying a liquid into gaps between the tips of the plurality of nano-fingers, and wherein evaporation of the liquid causes the tips of the plurality of nano-fingers to approach each other through capillary force.

12. The method according to claim 11, wherein the liquid comprises a plurality of probe molecules, wherein the plurality of probe molecules are to become trapped between the contacting Raman-active material nano-particles.

* * * * *